US012767937B2

(12) United States Patent
Jiang et al.

(10) Patent No.: US 12,767,937 B2
(45) Date of Patent: Oct. 20, 2026

(54) TAQ POLYMERASE MUTANT, AND PREPARATION METHOD THEREFOR AND USE THEREOF

(71) Applicant: DAAN GENE CO., LTD., Guangzhou (CN)

(72) Inventors: Xiwen Jiang, Guangzhou (CN); Aishan Liu, Guangzhou (CN); Wei Zhang, Guangzhou (CN); Xiaocheng Xie, Guangzhou (CN); Xuelan Lu, Guangzhou (CN)

(73) Assignee: DAAN GENE CO., LTD., Guangzhou (CN)

( * ) Notice: Subject to any disclaimer, the term of this patent is extended or adjusted under 35 U.S.C. 154(b) by 279 days.

(21) Appl. No.: 18/694,726

(22) PCT Filed: Jun. 22, 2022

(86) PCT No.: PCT/CN2022/100275
§ 371 (c)(1),
(2) Date: Mar. 22, 2024

(87) PCT Pub. No.: WO2023/098035
PCT Pub. Date: Jun. 8, 2023

(65) Prior Publication Data

US 2024/0392266 A1 Nov. 28, 2024

(30) Foreign Application Priority Data

Nov. 30, 2021 (CN) ......................... 202111442628.3

(51) Int. Cl.
*C12N 9/12* (2006.01)
*C12N 15/70* (2006.01)

(52) U.S. Cl.
CPC ........... *C12N 9/1252* (2013.01); *C12N 15/70* (2013.01); *C12Y 207/07007* (2013.01)

(58) Field of Classification Search
CPC .................. C12N 9/1252; C12N 15/70; C12Y 207/07007; C12Q 1/6848; C12R 2001/19; Y02A 50/30
See application file for complete search history.

(56) References Cited

FOREIGN PATENT DOCUMENTS

| | | | | | |
|---|---|---|---|---|---|
| CN | 110684752 A | | 1/2020 | | |
| CN | 111484987 A | | 8/2020 | | |
| CN | 112574971 A | * | 3/2021 | ............. | C12Q 1/686 |
| EP | 2554665 A2 | | 2/2013 | | |
| WO | 9709451 A1 | | 3/1997 | | |

OTHER PUBLICATIONS

UniProt, DPO1_THEAQ, Feb. 1, 1991, UniProt, 1-8 (Year: 1991).*
International Search Report (with English translation) and Written Opinion issued in PCT/CN2022/100275, dated Aug. 19, 2022, 13 pages provided.
Yasukawa, K. "DNA polymerase [Thermus thermophilus]", GenBank, Oct. 27, 2012, 1 page.

* cited by examiner

*Primary Examiner* — Sharmila G Landau
*Assistant Examiner* — Ashley T White
(74) *Attorney, Agent, or Firm* — HSML P.C.

(57) ABSTRACT

Provided are a Taq polymerase mutant, a preparation method therefor and the use thereof. The Taq polymerase mutant includes an amino acid sequence having at least 70% identity to the amino acid sequence shown in SEQ ID NO:2, wherein the amino acid sequence has mutations occurring at one or more positions selected from the group consisting of: P40, L125, G200, D335, G499, E634, F769 or a combination thereof. The provided Taq polymerase mutant has high amplification activity, can obtain more amplification products compared with wild-type Taq polymerase under the same number of PCR cycles, and moreover, is resistant to whole blood and high salt and has low 5'-3' exonuclease activity.

8 Claims, 3 Drawing Sheets

Specification includes a Sequence Listing.

SEQUENCE LISTING

```
<160> NUMBER OF SEQ ID NOS: 2

<210> SEQ ID NO 1
<211> LENGTH: 2499
<212> TYPE: DNA
<213> ORGANISM: Thermus aquaticus

<400> SEQUENCE: 1

atgcgtggca tgctgcctct gtttgaaccg aaaggccgcg tgttactggt tgatggccat      60

catctggcct atcgtacctt tcacgcactg aagggtctga ccacaagccg tggcgagccg     120

gttcaggccg tgtacggctt cgccaaaagc ctgctgaaag ccctgaaaga agacggcgat     180

gccgtgatcg tggttttcga cgccaaggca ccgagctttc gtcatgaggc ttatggtggc     240

tataaagccg gtcgcgcacc gacaccggag gatttcccgc gccagctggc cttaattaaa     300

gagctggtgg atctgttagg cctggcccgc ctggaggttc cgggttatga agccgacgac     360
```

```
gtgctggcca gcttagccaa gaaggcagag aaagagggct atgaggtgcg cattctgacc    420
gcagacaagg acctgtatca gctgctgagc gatcgcattc atgtgctgca tccggagggc    480
tacctgatta ccccggcctg gctgtgggaa aaatatggtc tgcgcccgga tcaatgggca    540
gattatcgcg cactgacagg cgatgaaagc gataacctgc cgggtgttaa aggcattggc    600
gagaagacag cacgtaagct gctggaagaa tggggtagcc tggaagccct gttaaagaac    660
ctggaccgtc tgaagccggc aatccgcgag aagattctgg cccacatgga tgatctgaag    720
ctgagttggg atctggccaa agttcgcaca gacttaccgc tggaagtgga ctttgccaag    780
cgtcgtgaac cggaccgcga acgtctgcgt gccttcttag aacgcctgga attcggtagc    840
ctgctgcacg aatttggtct gctggaaagc ccgaaagcct tagaagaagc tccgtggccg    900
cctccggaag gtgcctttgt tggctttgtt ctgagccgca aagagccgat gtgggcagat    960
ttactggccc tggccgcagc acgcggtggt cgtgttcatc gtgccccgga accgtataaa   1020
gccctgcgcg acctgaaaga ggcacgtggt ctgttagcaa aggacctgag cgtgttagca   1080
ctgcgtgaag gtctgggctt accgcctggt gatgatccga tgctgctggc ctacctgctg   1140
gacccgagca acaccacccc tgagggtgtg gcacgccgtt atggtggtga atggaccgag   1200
gaagcaggtg aacgcgccgc actgagtgag cgtctgtttg caaacctgtg ggcccgtctg   1260
gaaggcgagg aacgtctgct gtggctgtac cgcgaagtgg aacgcccgct gagcgccgtt   1320
ttagcccaca tggaggccac cggcgttcgc ttagatgtgg cctatctgcg cgccctgagc   1380
ctggaagttg cagaagaaat cgcccgtctg gaggcagagg tgtttcgttt agccggccat   1440
ccgttcaacc tgaatagccg cgaccagctg gaacgcgtgc tgtttgatga actgggctta   1500
ccggccattg gcaagaccga gaagaccggt aaacgtagta ccagtgcagc cgttctggaa   1560
gcactgcgtg aagcccaccc tattgtggaa aagattctgc aatatcgcga gttaaccaaa   1620
ctgaagagca cctacatcga tcctctgcct gatctgattc acccgcgcac cggtcgtctg   1680
cacacccgct ttaatcaaac agccacagcc accggtcgtc tgagcagcag cgatccgaac   1740
ttacagaaca ttccggtgcg caccccctctg ggccaacgca ttcgtcgcgc cttcattgcc  1800
gaagaaggct ggttactggt ggccctggac tacagccaga ttgagctgcg tgttttagcc   1860
catctgagcg gcgacgaaaa cctgattcgc gtgtttcaag agggccgcga tattcataca   1920
gagaccgcca gctggatgtt tggtgttcct cgcgaagccg ttgatccgct gatgcgccgc   1980
gcagccaaaa caattaactt cggtgtgctg tatggtatga gcgcccaccg tttaagccag   2040
gagctggcca ttccgtatga agaggcccag gcatttatcg agcgctactt ccagagtttc   2100
cctaaggtgc gtgcatggat cgagaaaaca ctggaggaag gtcgccgtcg tggctacgtg   2160
gaaaccctgt ttggccgccg tcgctatgtg ccggatctgg aagcccgcgt gaaaagcgtt   2220
cgtgaggcag cagagcgcat ggcatttaat atgccggtgc agggtaccgc agccgacctg   2280
atgaaactgg caatggtgaa gctgtttccg cgtctggaag agatgggcgc ccgcatgtta   2340
ctgcaggtgc acgacgaact ggttctggag gcaccgaaag aacgtgccga agcagtggca   2400
cgcctggcca aagaggttat ggaaggcgtt tatccgttag ccgttccgct ggaggtggag   2460
gttggcattg gcgaagactg gctgagtgca aaagaataa                          2499
```

<210> SEQ ID NO 2
<211> LENGTH: 832
<212> TYPE: PRT
<213> ORGANISM: Thermus aquaticus

<400> SEQUENCE: 2

-continued

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415
```

-continued

```
Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830
```

TAQ POLYMERASE MUTANT, AND PREPARATION METHOD THEREFOR AND USE THEREOF

CROSS-REFERENCE TO RELATED APPLICATION

This patent application claims priority to the Chinese patent application filed on Nov. 30, 2021, with application No. 202111442628.3 and title of "TAQ POLYMERASE MUTANT, AND PREPARATION METHOD THEREOF AND USE THEREOF", which is hereby incorporated by reference in its entirety.

TECHNICAL FIELD

The present invention relates to the field of PCR detection, in particular to Taq polymerase mutant and preparation methods and use thereof.

BACKGROUND

Taq polymerase is a heat-resistant DNA polymerase derived from the heat-resistant bacterium *Thermus aquaticus*, with a molecular weight of 94 KDa. In the presence of magnesium ions, its optimal reaction temperature is 75-80° C., and its active half-life is 40 minutes at 95° C. It has 5'-3' nucleic acid exonuclease activity. Because of its high temperature resistance, Taq polymerase is widely used in polymerase chain reaction (PCR) and is the enzyme of first choice for nucleic acid amplification and detection. Modern molecular biology testing techniques require increasing sensitivity, precision, and durability of the PCR reaction, and wild-type Taq polymerase cannot fully meet the needs of practical applications.

However, the poor tolerance of wild-type Taq polymerase to extreme conditions (e.g., high salt or whole blood) reduces its range of applicability, accuracy, and sensitivity, and does not allow it to fully meet the requirements of modern molecular bioassay techniques for PCR reactions. Furthermore, when PCR amplification is performed by dye method, the wild-type Taq polymerase in the system has 5'-3' exonuclease activity, which reduces the amplification efficiency in PCR amplification by dye method.

Therefore, it is important to develop a Taq polymerase mutant with low 5'-3' exonuclease activity, which is resistant to whole blood and high salt.

SUMMARY OF INVENTION

It is an object of the present invention to provide a Taq polymerase mutant.

It is another object of the present invention to provide a nucleic acid molecule encoding said Taq polymerase mutant.

It is another object of the present invention to provide a vector.

It is another object of the present invention to provide a host cell.

It is another object of the present invention to provide a method of preparing a Taq polymerase mutant.

It is another object of the present invention to provide a kit containing a Taq polymerase mutant.

In order to solve the above technical problem, a first aspect of the present invention provides a Taq polymerase mutant, wherein the Taq polymerase mutant comprises: an amino acid sequence having at least 70% identity to the amino acid sequence shown in SEQ ID NO:2, wherein the amino acid sequence being mutated at one or more positions selected from the group consisting of: P40, LI25, G200, G499, E634, F769, or a combination thereof.

In some preferred embodiments, the amino acid sequence is mutated at any four or more positions selected from the group consisting of P40W, LI251, G200M, G499K, E634G and F769I.

In some preferred embodiments, the amino acid sequence is mutated at positions in the following group: G499K, E634G and F769I; and the amino acid sequence is also mutated at any one or more positions selected from the group consisting of: P40W, L125I and G200M.

In some preferred embodiments, the amino acid sequence is mutated at positions in the following group: P40W, LI251, G200M, G499K, E634G and F769I.

In some preferred embodiments, the Taq polymerase mutant has a resistance to sodium chloride of not less than 70 mM, more preferably not less than 80 mM, more preferably not less than 90 mM, more preferably not less than 100 mM, more preferably not less than 130 mM, more preferably not less than 150 mM, and most preferably not less than 180 mM.

In some preferred embodiments, the Taq polymerase mutant has a resistance to potassium chloride of not less than 100 mM, more preferably not less than 110 mM, more preferably not less than 120 mM, more preferably not less than 130 mM, more preferably not less than 140 mM, more preferably not less than 150 mM, more preferably not less than 180 mM, more preferably not less than 190 mM, and most preferably not less than 200 mM.

In some preferred embodiments, the Taq polymerase mutant has a resistance to EDTA whole blood of not less than 5%, more preferably not less than 7%, more preferably not less than 10%, more preferably not less than 20%, more preferably not less than 30%, more preferably not less than 40%, and most preferably not less than 50%.

In some preferred embodiments, the Taq polymerase mutant has a resistance to heparin whole blood of not less than 1%, more preferably not less than 3%, more preferably not less than 5%, more preferably not less than 10%, more preferably not less than 20%, preferably not less than 30%, and most preferably not less than 35%.

```
SEQ ID NO: 1 (the DNA sequence of wild-type Taq
polymerase is as follows):
ATGCGTGGCATGCTGCCTCTGTTTGAACCGAAAGGCCGCGTGTTACTGGT

TGATGGCCATCATCTGGCCTATCGTACCTTTCACGCACTGAAGGGTCTGA

CCACAAGCCGTGGCGAGCCGGTTCAGGCCGTGTACGGCTTCGCCAAAAGC

CTGCTGAAAGCCCTGAAAGAAGACGGCGATGCCGTGATCGTGGTTTTCGA

CGCCAAGGCACCGAGCTTTCGTCATGAGGCTTATGGTGGCTATAAAGCCG

GTCGCGCACCGACACCGGAGGATTTCCCGCGCCAGCTGGCCTTAATTAAA

GAGCTGGTGGATCTGTTAGGCCTGGCCCGCCTGGAGGTTCCGGGTTATGA

AGCCGACGACGTGCTGGCCAGCTTAGCCAAGAAGGCAGAGAAAGAGGGC

TATGAGGTGCGCATTCTGACCGCAGACAAGGACCTGTATCAGCTGCTGAG

CGATCGCATTCATGTGCTGCATCCGGAGGGCTACCTGATTACCCCGGCCT

GGCTGTGGGAAAAATATGGTCTGCGCCCGGATCAATGGGCAGATTATCGC

GCACTGACAGGCGATGAAAGCGATAACCTGCCGGGTGTTAAAGGCATTG

GCGAGAAGACAGCACGTAAGCTGCTGGAAGAATgGGGTAgCCTGGAAGC
```

-continued

```
CCTGTTAAAGAACCTGGACCGTCTGAAGCCGGCAATCCGCGAGAAGATTC
TGGCCCACATGGATGATCTGAAGCTGAGTTGGGATCTGGCCAAAGTTCGC
ACAGACTTACCGCTGGAAGTGGACTTTGCCAAGCGTCGTGAACCGGACCG
CGAACGTCTGCGTGCCTTCTTAGAACGCCTGGAATTCGGTAGCCTGCTGC
ACGAATTTGGTCTGCTGGAAAGCCCGAAAGCCTTAGAAGAAGCTCCGTGG
CCGCCTCCGGAAGGTGCCTTTGTTGGCTTTGTTCTGAGCCGCAAAGAGCC
GATGTGGGCAGATTTACTGGCCCTGGCCGCAGCACGCGGTGGTCGTGTTC
ATCGTGCCCCGGAACCGTATAAAGCCCTGCGCGACCTGAAAGAGGCACG
TGGTCTGTTAGCAAAGGACCTGAGCGTGTTAGCACTGCGTGAAGGTCTGG
GCTTACCGCCTGGTGATGATCCGATGCTGCTGGCCTACCTGCTGGACCCG
AGCAACACCACCCCTGAGGGTGTGGCACGCCGTTATGGTGGTGAATGGAC
CGAGGAAGCAGGTGAACGCGCCGCACTGAGTGAGCGTCTGTTTGCAAAC
CTGTGGGGCCGTCTGGAAGGCGAGGAACGTCTGCTGTGGCTGTACCGCGA
AGTGGAACGCCCGCTGAGCGCCGTTTTAGCCCACATGGAGGCCACCGGCG
TTCGCTTAGATGTGGCCTATCTGCGCGCCCTGAGCCTGGAAGTTGCAGAA
GAAATCGCCCGTCTGGAGGCAGAGGTGTTTCGTTTAGCCGGCCATCCGTT
CAACCTGAATAGCCGCGACCAGCTGGAACGCGTGCTGTTTGATGAACTGG
GCTTACCGGCCATTGGCAAGACCGAGAAGACCGGTAAACGTAGTACCAG
TGCAGCCGTTCTGGAAGCACTGCGTGAAGCCCACCCTATTGTGGAAAAGA
TTCTGCAATATCGCGAGTTAACCAAACTGAAGAGCACCTACATCGATCCT
CTGCCTGATCTGATTCACCCGCGCACCGGTCGTCTGCACACCCGCTTTAA
TCAAACAGCCACAGCCACCGGTCGTCTGAGCAGCAGCGATCCGAACTTAC
AGAACATTCCGGTGCGCACCCCTCTGGGCCAACGCATTCGTCGCGCCTTC
ATTGCCGAAGAAGGCTGGTTACTGGTGGCCCTGGACTACAGCCAGATTGA
GCTGCGTGTTTTAGCCCATCTGAGCGGCGACGAAAACCTGATTCGCGTGT
TTCAAGAGGGCCGCGATATTCATACAGAGACCGCCAGCTGGATGTTTGGT
GTTCCTCGCGAAGCCGTTGATCCGCTGATGCGCCGCGCAGCCAAAACAAT
TAACTTCGGTGTGCTGTATGGTATGAGCGCCCACCGTTTAAGCCAGGAGC
TGGCCATTCCGTATGAAGAGGCCCAGGCATTTATCGAGCGCTACTTCCAG
AGTTTCCCTAAGGTGCGTGCATGGATCGAGAAAACACTGGAGGAAGGTC
GCCGTCGTGGCTACGTGGAAACCCTGTTTGGCCGCCGTCGCTATGTGCCG
GATCTGGAAGCCCGCGTGAAAAGCGTTCGTGAGGCAGCAGAGCGCATGG
CATTTAATATGCCGGTGCAGGGTACCGCAGCCGACCTGATGAAACTGGCA
ATGGTGAAGCTGTTTCCGCGTCTGGAAGAGATGGGCGCCCGCATGTTACT
GCAGGTGCACGACGAACTGGTTCTGGAGGCACCGAAAGAACGTGCCGAA
GCAGTGGCACGCCTGGCCAAAGAGGTTATGGAAGGCGTTTATCCGTTAGC
CGTTCCGCTGGAGGTGGAGGTTGGCATTGGCGAAGACTGGCTGAGTGCAA
AAGAATAA
```

-continued

SEQ ID NO:2 (the amino acid sequence of wild-type Taq polymerase is as follows):

```
MRGMLPLFEPKGRVLLVDGHHLAYRTFHALKGLTTSRGEPVQAVYGFAKS
LLKALKEDGDAVIVVFDAKAPSFRHEAYGGYKAGRAPTPEDFPRQLALIK
ELVDLLGLARLEVPGYEADDVLASLAKKAEKEGYEVRILTADKDLYQLLS
DRIHVLHPEGYLITPAWLWEKYGLRPDQWADYRALTGDESDNLPGVKGIG
EKTARKLLEEWGSLEALLKNLDRLKPAIREKILAHMDDLKLSWDLAKVRT
DLPLEVDFAKRREPDRERLRAFLERLEFGSLLHEFGLLESPKALEEAPWP
PPEGAFVGFVLSRKEPMWADLLALAAARGGRVHRAPEPYKALRDLKEARG
LLAKDLSVLALREGLGLPPGDDPMLLAYLLDPSNTTPEGVARRYGGEWTE
EAGERAALSERLFANLWGRLEGEERLLWLYREVERPLSAVLAHMEATGVR
LDVAYLRALSLEVAEEIARLEAEVFRLAGHPFNLNSRDQLERVLFDELGL
PAIGKTEKTGKRSTSAAVLEALREAHPIVEKILQYRELTKLKSTYIDPLP
DLIHPRTGRLHTRFNQTATATGRLSSSDPNLQNIPVRTPLGQRIRRAFIA
EEGWLLVALDYSQIELRVLAHLSGDENLIRVFQEGRDIHTETASWMFGVP
REAVDPLMRRAAKTINFGVLYGMSAHRLSQELAIPYEEAQAFIERYFQSF
PKVRAWIEKTLEEGRRRGYVETLFGRRRYVPDLEARVKSVREAAERMAFN
MPVQGTAADLMKLAMVKLFPRLEEMGARMLLQVHDELVLEAPKERAEAVA
RLAKEVMEGVYPLAVPLEVEVGIGEDWLSAKE
```

In some preferred embodiments, the amino acid sequence has one or more mutations selected from the group consisting of: P40W, LI251, G200M, G499K, E634G and F769I.

In some preferred embodiments, the Taq polymerase mutant comprises an amino acid sequence having at least 80% identity with the amino acid sequence shown in SEQ ID NO:1; more preferably, the Taq polymerase mutant comprises an amino acid sequence having at least 90% identity with the amino acid sequence shown in SEQ ID NO:1; more preferably, the Taq polymerase mutant comprises an amino acid sequence having at least 95% identity with the amino acid sequence shown in SEQ ID NO:1.

A second aspect of the present invention further provides a nucleotide molecule, wherein the nucleotide molecule encodes a Taq polymerase mutant described in the first aspect of the present invention.

A third aspect of the present invention further provides a vector comprising the nucleotide molecule described in the second aspect of the present invention.

A fourth aspect of the present invention further provides a host cell, wherein the host cell contains a nucleotide molecule described in the second aspect of the present invention, or its chromosome is integrated with a nucleotide molecule described in the second aspect of the present invention.

In some preferred embodiments, wherein the host cell is a prokaryotic cell, or an eukaryotic cell.

In some preferred embodiments, wherein the prokaryotic cell is *E. coli*.

In some preferred embodiments, wherein the eukaryotic cell is a yeast cell.

A fifth aspect of the present invention further provides a kit containing a Taq polymerase mutant described in the first aspect of the present invention.

A sixth aspect of the present invention further provides a method of preparing the Taq polymerase mutant described in the first aspect of the present invention, wherein the method comprising the steps of.

(i) culturing the host cell described in the fourth aspect of the present invention under suitable conditions so as to express the Taq polymerase mutant; and (ii) isolating the Taq polymerase mutant.

A seventh aspect of the present invention also provides uses for the kit described in the fifth aspect of the present invention, which is used for DNA sequencing, DNA labeling, primer extension, amplification, and the like.

The present invention has at least the following advantages over the prior art:

(1) The Taq polymerase mutants of provided by the present invention has high amplification activity, and can obtain more amplification products than the wild-type Taq polymerase at the same number of PCR cycles;

(2) The Taq polymerase mutant provided by the present invention is resistant to both whole blood and high salt;

(3) The Taq polymerase mutant provided by the present invention has low 5'-3' exonuclease activity and is suitable for dye-based PCR systems.

It should be understood that each technical feature of above description and that of the following description (e.g., Examples) may be combined with each other to constitute a new or preferred technical solution. Because of the limitation of space, they will not be repeated herein.

DESCRIPTION OF DRAWINGS

One or more embodiments are exemplarily illustrated by the figures in the accompanying drawings, which do not constitute a limitation of the embodiments.

EMBODIMENTS

Figure 1:
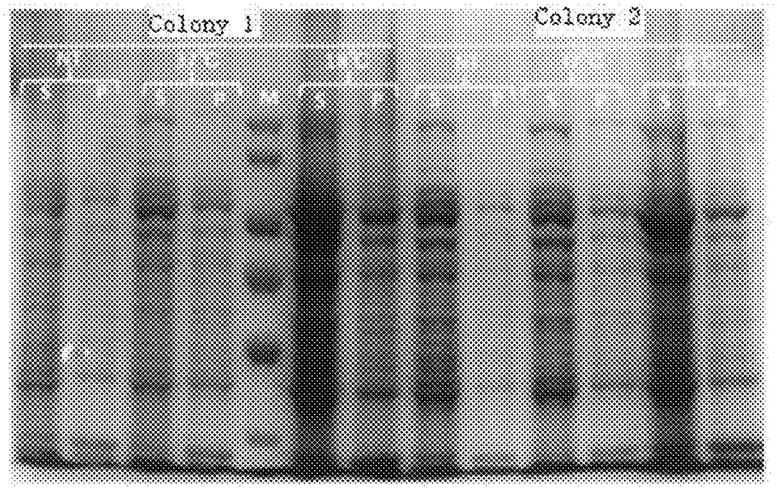
FIG. 1 is a graph of the results of SDS-PAGE identification of the target proteins according to the examples of the present invention.

The wild-type Taq polymerase has difficulty in amplification under some extreme conditions where its polymerization activity is low, such as high salt, whole blood environments. Although attempts have been made in the prior art to mutate wild-type Taq polymerase to enhance its resistance to extreme conditions, but with little success. Through extensive and in-depth research, the present inventors have screened out Taq polymerase mutants with good performance by applying enzyme site mutation technology. The screened Taq polymerase mutants have good polymerization activity, good resistance to high salt and whole blood, and are suitable for clinical use. In addition, the Taq polymerase mutants of the present invention have low 5'-3' exonuclease activity, which is very suitable for dye-based PCR system.

Some preferred embodiments of the present invention provide a Taq polymerase mutant, which comprises: an amino acid sequence having at least 70% identity to the amino acid sequence shown in SEQ ID NO:2, wherein the amino acid sequence is mutated at one or more positions selected from the group consisting of: P40, LI25, G200, G499, E634, F769, or a combination thereof.

In some preferred embodiments, the amino acid sequence has any one or more mutations selected from the group consisting of P40W, LI251, G200M, G499K, E634G and F769I.

In some preferred embodiments, the amino acid sequence is mutated at positions in the following group: G499K, E634G and F769I; and the amino acid sequence is also mutated at any one or more positions selected from the following group: P40W, L125I and G200M.

In some preferred embodiments, the amino acid sequence is mutated at positions in the following group: P40W, LI251, G200M, G499K, E634G and F769I.

In some preferred embodiments, the Taq polymerase mutant has a resistance to sodium chloride of not less than 70 mM, more preferably not less than 80 mM, more preferably not less than 90 mM, more preferably not less than 100 mM, more preferably not less than 130 mM, more preferably not less than 150 mM, and most preferably not less than 180 mM.

In some preferred embodiments, the Taq polymerase mutant has a resistance to potassium chloride of not less than 100 mM, more preferably not less than 110 mM, more preferably not less than 120 mM, more preferably not less than 130 mM, more preferably not less than 140 mM, more preferably not less than 150 mM, more preferably not less than 180 mM, more preferably not less than 190 mM, and most preferably not less than 200 mM.

In some preferred embodiments, the Taq polymerase mutant has a resistance to EDTA whole blood of not less than 5% (the percentage here refers to the percentage of plasma volume to the total volume of the PCR solution system), more preferably not less than 7%, more preferably not less than 10%, more preferably not less than 20%, more preferably not less than 30%, more preferably not less than 40%, and most preferably not less than 50%.

In some preferred embodiments, the Taq polymerase mutant has a resistance to heparin whole blood of not less than 1% (the percentage here refers to the percentage of plasma volume to the total volume of the PCR solution system), more preferably not less than 3%, more preferably not less than 5%, more preferably not less than 10%, more preferably not less than 20%, preferably not less than 30%, and most preferably not less than 35%.

```
SEQ ID NO: 1 (the DNA sequence of wild-type Taq
polymerase is as follows):
ATGCGTGGCATGCTGCCTCTGTTTGAACCGAAAGGCCGCGTGTTACTGGT

TGATGGCCATCATCTGGCCTATCGTACCTTTCACGCACTGAAGGGTCTGA

CCACAAGCCGTGGCGAGCCGGTTCAGGCCGTGTACGGCTTCGCCAAAAGC
```

-continued

```
CTGCTGAAAGCCCTGAAAGAAGACGGCGATGCCGTGATCGTGGTTTTCGA
CGCCAAGGCACCGAGCTTTCGTCATGAGGCTTATGGTGGCTATAAAGCCG
GTCGCGCACCGACACCGGAGGATTTCCCGCGCCAGCTGGCCTTAATTAAA
GAGCTGGTGGATCTGTTAGGCCTGGCCCGCCTGGAGGTTCCGGGTTATGA
AGCCGACGACGTGCTGGCCAGCTTAGCCAAGAAGGCAGAGAAAGAGGGC
TATGAGGTGCGCATTCTGACCGCAGACAAGGACCTGTATCAGCTGCTGAG
CGATCGCATTCATGTGCTGCATCCGGAGGGCTACCTGATTACCCCGGCCT
GGCTGTGGGAAAAATATGGTCTGCGCCCGGATCAATGGGCAGATTATCGC
GCACTGACAGGCGATGAAAGCGATAACCTGCCGGGTGTTAAAGGCATTG
GCGAGAAGACAGCACGTAAGCTGCTGGAAGAATgGGGTAgCCTGGAAGC
CCTGTTAAAGAACCTGGACCGTCTGAAGCCGGCAATCCGCGAGAAGATTC
TGGCCCACATGGATGATCTGAAGCTGAGTTGGGATCTGGCCAAAGTTCGC
ACAGACTTACCGCTGGAAGTGGACTTTGCCAAGCGTCGTGAACCGGACCG
CGAACGTCTGCGTGCCTTCTTAGAACGCCTGGAATTCGGTAGCCTGCTGC
ACGAATTTGGTCTGCTGGAAAGCCCGAAAGCCTTAGAAGAAGCTCCGTGG
CCGCCTCCGGAAGGTGCCTTTGTTGGCTTTGTTCTGAGCCGCAAAGAGCC
GATGTGGGCAGATTTACTGGCCCTGGCCGCAGCACGCGGTGGTCGTGTTC
ATCGTGCCCCGGAACCGTATAAAGCCCTGCGCGACCTGAAAGAGGCACG
TGGTCTGTTAGCAAAGGACCTGAGCGTGTTAGCACTGCGTGAAGGTCTGG
GCTTACCGCCTGGTGATGATCCGATGCTGCTGGCCTACCTGCTGGACCCG
AGCAACACCACCCCTGAGGGTGTGGCACGCCGTTATGGTGGTGAATGGAC
CGAGGAAGCAGGTGAACGCGCCGCACTGAGTGAGCGTCTGTTTGCAAAC
CTGTGGGGCCGTCTGGAAGGCGAGGAACGTCTGCTGTGGCTGTACCGCGA
AGTGGAACGCCCGCTGAGCGCCGTTTTAGCCCACATGGAGGCCACCGGCG
TTCGCTTAGATGTGGCCTATCTGCGCGCCCTGAGCCTGGAAGTTGCAGAA
GAAATCGCCCGTCTGGAGGCAGAGGTGTTTCGTTTAGCCGGCCATCCGTT
CAACCTGAATAGCCGCGACCAGCTGGAACGCGTGCTGTTTGATGAACTGG
GCTTACCGGCCATTGGCAAGACCGAGAAGACCGGTAAACGTAGTACCAG
TGCAGCCGTTCTGGAAGCACTGCGTGAAGCCCACCCTATTGTGGAAAAGA
TTCTGCAATATCGCGAGTTAACCAAACTGAAGAGCACCTACATCGATCCT
CTGCCTGATCTGATTCACCCGCGCACCGGTCGTCTGCACACCCGCTTTAA
TCAAACAGCCACAGCCACCGGTCGTCTGAGCAGCAGCGATCCGAACTTAC
AGAACATTCCGGTGCGCACCCCTCTGGGCCAACGCATTCGTCGCGCCTTC
ATTGCCGAAGAAGGCTGGTTACTGGTGGCCCTGGACTACAGCCAGATTGA
GCTGCGTGTTTTAGCCCATCTGAGCGGCGACGAAAACCTGATTCGCGTGT
TTCAAGAGGGCCGCGATATTCATACAGAGACCGCCAGCTGGATGTTTGGT
GTTCCTCGCGAAGCCGTTGATCCGCTGATGCGCCGCGCAGCCAAAACAAT
TAACTTCGGTGTGCTGTATGGTATGAGCGCCCACCGTTTAAGCCAGGAGC
TGGCCATTCCGTATGAAGAGGCCCAGGCATTTATCGAGCGCTACTTCCAG
AGTTTCCCTAAGGTGCGTGCATGGATCGAGAAAACACTGGAGGAAGGTC
```

-continued

```
GCCGTCGTGGCTACGTGGAAACCCTGTTTGGCCGCCGTCGCTATGTGCCG
GATCTGGAAGCCCGCGTGAAAAGCGTTCGTGAGGCAGCAGAGCGCATGG
CATTTAATATGCCGGTGCAGGGTACCGCAGCCGACCTGATGAAACTGGCA
ATGGTGAAGCTGTTTCCGCGTCTGGAAGAGATGGGCGCCCGCATGTTACT
GCAGGTGCACGACGAACTGGTTCTGGAGGCACCGAAAGAACGTGCCGAA
GCAGTGGCACGCCTGGCCAAAGAGGTTATGGAAGGCGTTTATCCGTTAGC
CGTTCCGCTGGAGGTGGAGGTTGGCATTGGCGAAGACTGGCTGAGTGCAA
AAGAATAA
```

SEQ ID NO:2 (the amino acid sequence of wild-type Taq polymerase is as follows):

```
MRGMLPLFEPKGRVLLVDGHHLAYRTFHALKGLTTSRGEPVQAVYGFAKS
LLKALKEDGDAVIVVFDAKAPSFRHEAYGGYKAGRAPTPEDFPRQLALIK
ELVDLLGLARLEVPGYEADDVLASLAKKAEKEGYEVRILTADKDLYQLLS
DRIHVLHPEGYLITPAWLWEKYGLRPDQWADYRALTGDESDNLPGVKGIG
EKTARKLLEEWGSLEALLKNLDRLKPAIREKILAHMDDLKLSWDLAKVRT
DLPLEVDFAKRREPDRERLRAFLERLEFGSLLHEFGLLESPKALEEAPWP
PPEGAFVGFVLSRKEPMWADLLALAAARGGRVHRAPEPYKALRDLKEARG
LLAKDLSVLALREGLGLPPGDDPMLLAYLLDPSNTTPEGVARRYGGEWTE
EAGERAALSERLFANLWGRLEGEERLLWLYREVERPLSAVLAHMEATGVR
LDVAYLRALSLEVAEEIARLEAEVFRLAGHPFNLNSRDQLERVLFDELGL
PAIGKTEKTGKRSTSAAVLEALREAHPIVEKILQYRELTKLKSTYIDPLP
DLIHPRTGRLHTRFNQTATATGRLSSSDPNLQNIPVRTPLGQRIRRAFIA
EEGWLLVALDYSQIELRVLAHLSGDENLIRVFQEGRDIHTETASWMFGVP
REAVDPLMRRAAKTINFGVLYGMSAHRLSQELAIPYEEAQAFIERYFQSF
PKVRAWIEKTLEEGRRRGYVETLFGRRRYVPDLEARVKSVREAAERMAFN
MPVQGTAADLMKLAMVKLFPRLEEMGARMLLQVHDELVLEAPKERAEAVA
RLAKEVMEGVYPLAVPLEVEVGIGEDWLSAKE
```

In some preferred embodiments, the Taq polymerase mutant comprises an amino acid sequence having at least 80% identity with the amino acid sequence shown in SEQ ID NO:1; more preferably, the Taq polymerase mutant comprises an amino acid sequence having at least 90% identity with the amino acid sequence shown in SEQ ID NO:1; more preferably, the Taq polymerase mutant comprises an amino acid sequence having at least 95% identity with the amino acid sequence shown in SEQ ID NO:1.

Some preferred embodiments of the present invention provide a nucleotide molecule, wherein the nucleotide molecule encodes a Taq polymerase mutant described in the first aspect of the present invention.

Some preferred embodiments of the present invention provide a vector comprising the nucleotide molecule described in the second aspect of the present invention.

Some preferred embodiments of the present invention provide a host cell, wherein the host cell contains a nucleotide molecule described in the second aspect of the present invention, or its chromosome is integrated with a nucleotide molecule described in the second aspect of the present invention.

In some preferred embodiments, the host cell is a prokaryotic cell, or an eukaryotic cell.

In some preferred embodiments, the prokaryotic cell is *E. coli.*

In some preferred embodiments, the eukaryotic cell is a yeast cell.

Some preferred embodiments of the present invention provide a kit containing a Taq polymerase mutant described in the first aspect of the present invention.

Some preferred embodiments of the present invention provide a method of preparing the Taq polymerase mutant described in the first aspect of the present invention, wherein the method comprises the steps of:

(i) culturing the host cell described in the fourth aspect of the present invention under suitable conditions so as to express the Taq polymerase mutant; and (ii) isolating the Taq polymerase mutant.

Some preferred embodiments of the present invention provide uses for the kit described in the fifth aspect of the present invention, which is used for DNA sequencing, DNA labeling, primer extension, amplification, and the like.

Terms

As used herein, the term "amino acid" in its broadest sense refers to any compound and/or substance that can be incorporated into a polypeptide chain. In some embodiments, the amino acid has the general structure of H2N—C(H)(R)—COOH. In some embodiments, the amino acid is a naturally occurring amino acid. In some embodiments, the amino acid is a synthetic amino acid; in some embodiments, the amino acid is a D-amino acid; in some embodiments, the amino acid is an L-amino acid. A "standard amino acid" typically refers to any of the twenty standard L-amino acids found in naturally occurring peptides. A "non-standard amino acid" is any amino acid other than a standard amino acid, whether prepared synthetically or obtained from natural sources.

As used herein, "synthetic amino acid" includes chemically modified amino acids, including, but not limited to, salts, amino acid derivatives (e.g., amides) and/or substituents. Amino acids, including carboxyl and/or amino-terminal amino acids in peptides, can be modified by methylation, amidation, acetylation, and/or substitution with other chemicals without adversely affecting their activity. The amino acids may have disulfide bonds. The term "amino acid" is used interchangeably with "amino acid residue" and may refer to free amino acids and/or amino acid residues of peptides. Whether the term refers to free amino acids or peptide residues, it will be apparent from the context in which the term is used. It should be noted that all amino acid residue sequences are represented herein by the left-right orientation of the formula in the conventional direction of amino terminus to carboxy terminus.

As used herein, the term "mutation" refers to the introduction of a change in the parental sequence, including, but not limited to, substitutions, insertions, deletions (including truncations). Consequences of a mutation include, but are not limited to, the occurrence of a new characteristic, property, function, phenotype or trait not found in the protein encoded by the parental sequence. The term "mutant" refers to a modified protein, wherein the modified protein exhibits altered characteristics when compared to the parental protein.

As used herein, the term "% homology" is used herein interchangeably with the term "% identity" and refers to the level of nucleic acid or amino acid sequence identity between nucleic acid sequences encoding any of the polypeptides of the invention or amino acid sequences of the polypeptides of the invention when compared using a sequence comparison program.

As used herein, the term "nucleotide" refers to a monomeric unit of DNA or RNA consisting of a sugar portion (pentose sugar), a phosphate ester, and a nitrogen-containing heterocyclic base. The base is attached to the sugar portion via the glycosidic carbon (the 1' carbon of the pentose sugar), and the combination of the base and the sugar is a nucleoside. When a nucleoside comprises a phosphate group bonded to the 3' or 5'-position of the pentose sugar, it is called a nucleotide. Sequences of operably linked nucleotides are commonly referred to herein as "base sequences" or "nucleotide sequence juxtapositions" and are represented herein in such a form that their left-to-right orientation is in the conventional direction from 5'-terminal to 3'-terminal.

As used herein, the term "vector" refers to a nucleoside construct designed for transferring between different host cells. The term "expression vector" refers to a vector that is capable of incorporating and expressing a heterologous DNA fragment in a foreign cell. Many prokaryotic and eukaryotic expression vectors are commercially available. The selection of suitable expression vectors is within the knowledge of those skilled in the art.

As used herein, the term "host cell" refers to a cell that has been invaded by a target gene, wherein the target gene can invade the cell in the form of a vector (e.g., a virus, chromosome, or plasmid) for replication.

As used herein, the term "chromosomal integration" refers to integration by homologous recombination of multiple copies of the target gene into a sufficiently defined sites.

Preparation of Taq Polymerase Mutants

The Taq polymerase gene sequences of the present invention can be obtained by conventional methods available to those of ordinary skill in the art, such as total synthesis or PCR synthesis. A preferred synthesis method is asymmetric PCR. Asymmetric PCR is a method in which a large amount of single stranded DNA (ssDNA) is produced after PCR amplification using an unequal pair of primers. This pair of primers are called a non-restriction primer and a restriction primer, and their ratio is generally 50-100:1. During the first 10-15 cycles of the PCR reaction, the amplification product is mainly double-stranded DNA, but when the restriction primer (a low concentration primer) is depleted, the non-restriction primer (a high concentration primer) guided PCR produces a large amount of single-stranded DNA. Primers for PCR can be appropriately selected based on the sequence information of the present invention disclosed herein and can be synthesized by conventional methods. Amplified DNA/RNA fragments can be separated and purified by conventional methods such as gel electrophoresis.

The Taq polymerase mutants of the present invention can be expressed or produced by conventional recombinant DNA techniques comprising the steps of:

(1) transforming or transducing a suitable host cell with a polynucleotide encoding a protein of the invention, or with a recombinant expression vector containing the polynucleotide;

(2) culturing the host cells in a suitable medium;

(3) isolating and purifying the target protein from the medium or cells to obtain a Taq polymerase mutant.

Methods known to those skilled in the art can be used to construct expression vectors containing DNA sequences encoding the Taq polymerase mutants of the present invention and suitable transcriptional/translational control signals, preferably the commercially available vector: pET28. These methods include in vitro recombinant DNA techniques, DNA synthesis techniques, in vivo recombination techniques and the like. The DNA sequence can be effectively attached to the appropriate promoter in the expression vector to direct mRNA synthesis. The expression vector also includes a ribosome binding site for translation initiation and a transcription terminator. In addition, the expression vector preferably comprises one or more selective marker genes to provide phenotypic traits for selection of host cells for transformation.

The recombinant vector comprises in the 5' to 3' direction: a promoter, a target gene and a terminator. If desired, the recombinant vector may also include the following elements: a protein purification tag; a 3' polynucleotide signal; a nontranslated nucleic acid sequence; a transport and targeting nucleic acid sequence; a selection marker (antibiotic resistance gene, fluorescent protein, etc.); an enhancer; or an operon.

Methods for preparing recombinant vectors are well known to those of ordinary skill in the art. Expression vectors may be a bacterial plasmid, phage, yeast plasmid, plant cell virus, mammalian cell virus, or other vectors. In short, any plasmid and vector can be employed as long as it is capable of replicating and stabilizing in the host.

A person of ordinary skill in the art may employ well known methods for constructing a vector containing a promoter of the present invention and/or a target gene sequence of the present invention. These methods include in vitro recombinant DNA techniques, DNA synthesis techniques, in vivo recombination, and the like.

The expression vectors of the present invention, can be used to transform appropriate host cells to cause the host to transcribe a target RNA or express a target protein. The host cell may be a prokaryotic cell, such as *Escherichia coli, Corynebacterium glutamicum, Brevibacterium flavum, Streptomyces* spp. and *Agrobacterium* spp.; or a lower eukaryotic cell, such as a yeast cell; or a higher eukaryotic cell, such as a plant cell. One of ordinary skill in the art knows how to select the appropriate vector and host cell. Transformation of host cells with recombinant DNA can be performed by conventional techniques known to those of skill in the art. When the host is a prokaryote (e.g., *E. coli*), it can be treated with $CaCl_2$). Electroporation can also be used. When the host is eukaryotic, the following DNA transfection methods are available: calcium phosphate co-precipitation, conventional mechanical methods (e.g., microinjection, electroporation, liposome packaging, etc.). Transformation of plants can also be performed using *Agrobacterium* transformation or gene gun transformation methods, such as leaf disk method, young embryo transformation method, bud immersion method, etc. For transformed plant cells, tissues or organs, they can be regenerated into plants by conventional methods to obtain transgenic plants.

In order to make the objects, technical solutions and advantages of the embodiments of the present invention clearer, the present invention is further elaborated below in connection with specific examples. It should be understood that these examples are used only to illustrate the present invention and are not intended to limit the scope of the present invention. The experimental methods for which specific conditions are not indicated in the following examples, and the experimental methods for which detailed conditions are not indicated in the following examples, are generally in accordance with conventional conditions such as those described in Sambrook. J et al. (ed.) Molecular Cloning: A Laboratory Manual, by U.S.A. (Translated by Huang Peitang et al., Beijing: Science Press, 2002), or in accordance with the conditions recommended by the manufacturer. Unless otherwise indicated, percentages and parts are weight percentages and weight parts. The experimental materials and reagents used in the following examples are available from commercially available sources if not otherwise indicated.

Unless otherwise indicated, technical and scientific terms used herein have the same meanings as are commonly understood by one of ordinary skill in the art to which this application belongs, and it is to be noted that the terms used herein are intended only to describe specific embodiments and is not intended to limit the exemplary embodiments of the present application.

Example 1: Preparation of Taq Polymerase Mutants Taq-aCb and Taq-aCb

Mut

Steps for the preparation of Taq polymerase mutants.

Step 1: Taq-aCb mutant plasmid was prepared by using wild-type Taq polymerase expression vector as template and QuikChange Lightning Multi-site Mutagenesis Kit, in which the wild-type expression vector was preserved by Guangzhou Daan Gene Co, and the vector was pET28a with His6 tag at the N-terminal. The mutant plasmids were sent for sequencing, and the sequencing results indicated that the mutant vectors were successfully constructed.

Step 2: Transformation of *E. coli* BL21 (DE3) with the Recombinant Plasmid

Under ice bath conditions, 1 μL plasmid was taken and added to 30 μL *Escherichia coli* BL21 (DE3). After placing in an ice bath for 20 minutes, it was heat shocked in the 42° C. water bath for 45 seconds and immediately transferred to ice for 2 minutes. 400 μL SOC medium without antibiotics was added, and subjected to 37° C., 220 rmp shaking culture for 50 minutes. 100 μL of the bacterial solution was spread evenly onto LB plates containing 100 μg/mL kanamycin and incubated overnight in an incubator at 37° C.

Step 3: Expression of Target Protein

The obtained monoclones in step 2 were picked and aseptically inoculated in TB medium containing 100 μg/mL kanamycin, incubated at 37° C. and 220 rpm with shaking until the OD600 was between 0.6 and 0.8, and induced with IPTG (final concentration of 0.1 mM), and left to be incubated overnight at 37° C. and 18° C. with shaking, respectively. The group without IPTG was used as a control and incubated at 37° C. for 3 h. The experiment was repeated once for each group. The samples were ultrasonically broken and analyzed by SDS-PAGE, and the results are shown in FIG. 1.

According to FIG. 1, a large amount of soluble proteins can be expressed in the supernatant of TB medium at 18° C., and the amount of soluble proteins accounted for more than 90% of the total amount of target proteins, and the molecular weight of the proteins was about 100 Kda.

Step 4: Purification of Taq-aCb

Shake flasks with 1.5 L of bacteriophage in TB medium were incubated, and the expression conditions were the same as those for the target proteins in step 3). The bacterium were collected by centrifugation, the wet weight of the two proteins was about 30 g. About 4 g of bacteriophage was weighed, 35 ml of Lysis Buffer was added and resuspend on ice. After ultrasonication, centrifugation at 20,000 rpm for 30 min at 4° C. was performed, the supernatant was filtered through a 0.22 μm needle filter to obtain the supernatant. The supernatant was subjected to affinity chromatography using a Ni-Column, and the linear elution was carried out using 0-60% Buffer B, and the eluate of the eluted main peak was taken and subjected to ion-exchange elution using a His- Trap™ Q-HP Purification Column, and the linear elution was carried out using 0-60% Buffer C.

Figure 2:
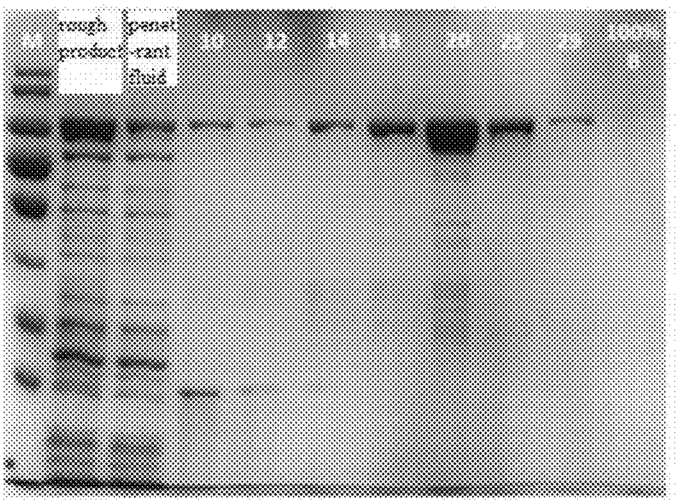
FIG. 2 is an electropherogram of Taq-aCb protein Nl column purification according to the examples of the present invention.
Figure 3:
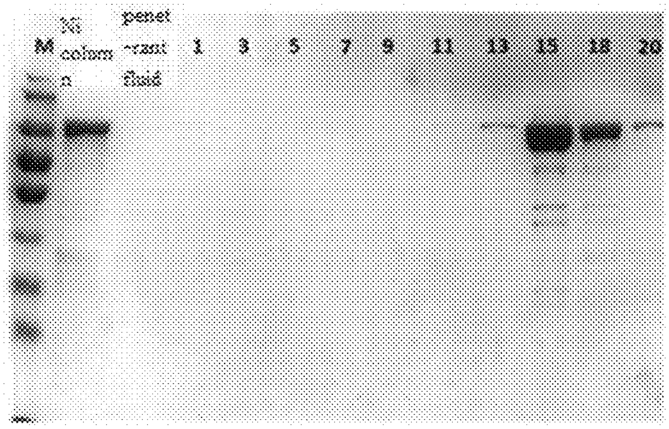
FIG. 3 is a graph of Taq-aCb protein Q-column purification electrophoresis according to the examples of the present invention.

The electropherograms are shown in FIGS. 2 and 3. The expression content of the target protein was calculated. The expression amount of Taq-aCb was 1.46 mg/mL. In this case, the concentration of the solution used was as follows:

Buffer B: 50 mM Tris, 50 mM NaCl, 500 mM Imidazole, 5% Glycerol, pH8.5;

Lysis Buffer: 50 mM Tris, 300 mM NaCl, 5% Glycerol, pH8.5;

Buffer C: 100 mM Tris, 1M NaCl, 10% Glycerol, pH8.5.

Example 2: Test of NaCl Resistance of Taq-aCb

Different NaCl concentration gradient solutions were prepared (NaCl concentration gradient configurations are shown in Table 1 below), Buffer A and Buffer B were prepared (formulations of Buffer A and Buffer B are shown in Table 1 below), and the NaCl concentration gradient solutions were formed by mixing Buffer A and Buffer B in different ratios.

TABLE 1

| | NaCl concentration/mM | | | | | | | | | | |
|---|---|---|---|---|---|---|---|---|---|---|---|
| | 0 | 10 | 20 | 30 | 40 | 50 | 60 | 70 | 80 | 90 | 100 |
| Buffer A/μL | 0 | 1 | 2 | 3 | 4 | 5 | 6 | 7 | 8 | 9 | 10 |
| Buffer B/μL | 10 | 9 | 8 | 7 | 6 | 5 | 4 | 3 | 2 | 1 | 0 |

The resistance of Taq-aCb to NaCl was determined using wild-type Taq polymerase as a positive control.

The PCR reaction system was prepared according to the formulation in Table 2, in which the RV and M4 primers were purchased from TaKaRa, and the 5× Fast Taq Buffer, pUC19 plasmid were kept by Guangzhou Daan Gene Co. The amount of enzyme added was 5 U per 10 μL of PCR reaction system. pUC19 plasmid was used as the template for amplification experiments, and the PCR products were subjected to 2% agarose gel electrophoresis.

TABLE 2

| reagents | Buffer A | Buffer B |
|---|---|---|
| RV(10 pmol) | 1.2 μL | 1.2 μL |
| M4(10 pmol) | 1.2 μL | 1.2 μL |
| pUC19 plasmid | 6 μL | 6 μL |
| 5X Fast Taq Buffer | 12 μL | 12 μL |
| wild type Taq/ Taq 2C2/Taq 2C2 Mut | 30 U | 30 U |
| 1 M NaCl | 6 μL | 0 μL |
| $ddH_2O$ | 31.6 μL | 37.6 μL |

Figure 4:
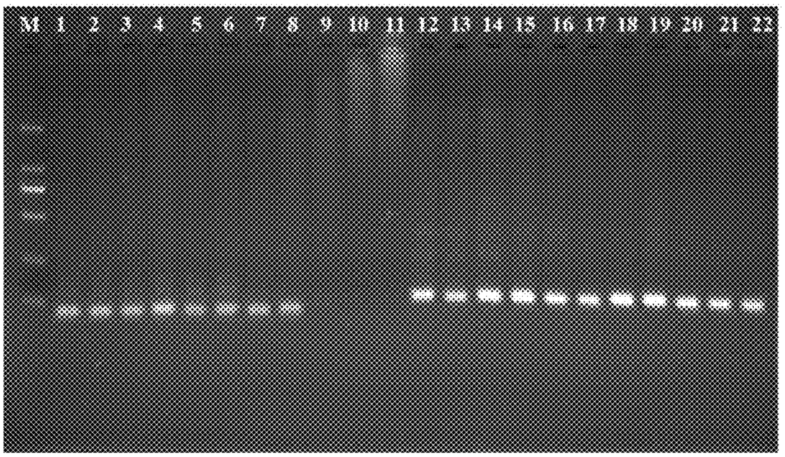
FIG. 4 is a graph showing the results of wild-type Taq polymerase and Taq-aCb anti-NaCl experiments according to the examples of the present invention.

Reaction conditions: 95° C. for 2 min, (95° C. for 15 s, 44° C. for 15 s, 72° C. for 1 min)×30 cycles, 72° C. for 1 min, and the electrophoresis results of amplified products are shown in FIG. 4.

As shown in FIG. 4, 1~11 are the PCR product lanes of wild-type Taq polymerase at 0, 10, 20, 30, 40, 50, 60, 70, 80, 90, and 100 mM NaCl concentration, respectively; 12~22 are the PCR product lanes of Taq-aCb at 0, 10, 20, 30, 40, 50, 60, 70, 80, 90, and 100 mM NaCl concentration, respectively. It can be seen that Taq-aCb has very good NaCl resistance compared with the wild type.

Figure 5:
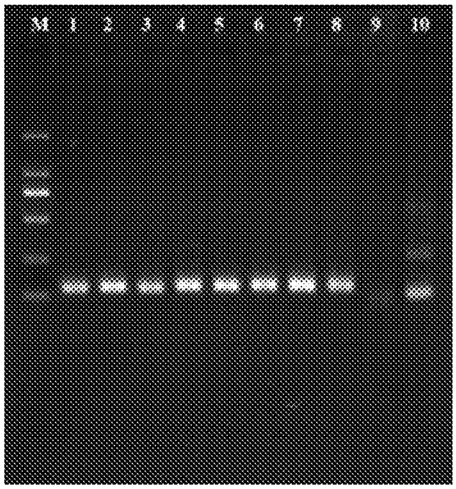
FIG. 5 is a graph showing the results of Taq-aCb anti-NaCl experiments according to the examples of the present invention.

Continuing to increase the NaCl concentration in the PCR reaction system to 110 mM-190 mM, the electrophoresis results of the amplified products were shown in FIG. 5.

As shown in FIG. 5, 1~9 are the PCR product lanes of Taq-aCb at 110, 120, 130, 140, 150, 160, 170, 180, and 190 mM NaCl concentration, respectively, and 10 is the positive control.

According to FIG. 5, the resistance of wild-type Taq enzyme to NaCl was 70 mM, and the resistance of Taq-aCb to NaCl reached 180 mM, so the Taq polymerase mutants had significantly improved NaCl resistance compared with wild-type Taq polymerase.

Example 3: Test of KCl Resistance of Taq-aCb

Different KCl concentration gradient solutions (Table 3) were prepared according to the method in Example 2, wherein NaCl was replaced with KCl in Buffer A.

TABLE 3

| | KCl concentration/mM | | | | | | | | | | |
|---|---|---|---|---|---|---|---|---|---|---|---|
| | 0 | 10 | 20 | 30 | 40 | 50 | 60 | 70 | 80 | 90 | 100 |
| Buffer A/μL | 0 | 1 | 2 | 3 | 4 | 5 | 6 | 7 | 8 | 9 | 10 |
| Buffer B/μL | 10 | 9 | 8 | 7 | 6 | 5 | 4 | 3 | 2 | 1 | 0 |

Figure 6:
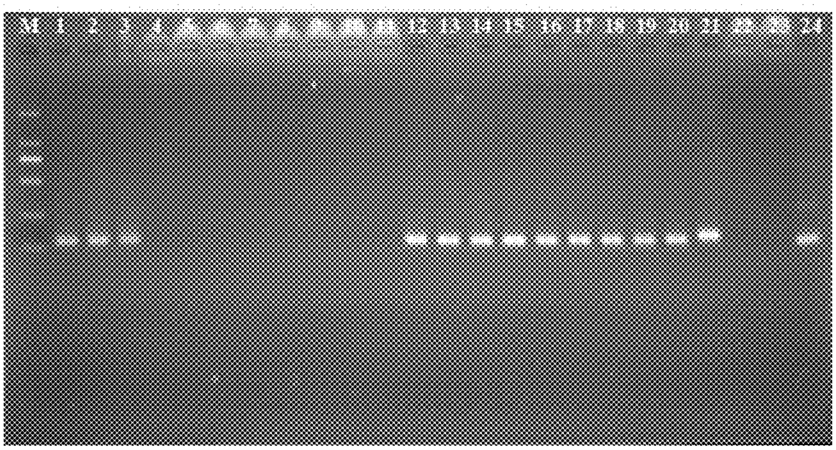
FIG. 6 is a graph showing the experimental results of wild-type Taq polymerase and Taq-aCb anti-KCl according to the examples of the present invention.

Taq-aCb resistance to KCl was tested according to the same method as in Example 2, and the electrophoresis results of the amplified products are shown in FIG. 6.

As in FIG. 6, 1~11 are the wild-type Taq polymerase PCR product lanes at KCl concentrations of 50, 80, 100, 150, 160, 170, 180, 190, 200, 250, and 300 mM, respectively; 13~18 are the PCR product lanes of Taq-aCb at KCl concentrations of 50, 80, 100, 150, 160, 170, 180, 190, 200, 250, and 300 mM, respectively; 12 and 24 are the positive controls.

According to FIG. 6, the resistance of wild-type Taq polymerase to KCl was 100 mM, and the Taq mutant Taq-aCb reached resistance to NaCl of 200 mM; thus, the Taq polymerase mutant showed significantly improved resistance to KCl as compared with the wild-type Taq polymerase.

Example 4: Test of EDTA Whole Blood Resistance of Taq-aCb

Different whole blood concentration gradient solutions (Table 4) were prepared according to the method in Example 2, wherein NaCl in Buffer A was replaced with EDTA whole blood. The volume fraction was calculated according to the volume of blood added to the PCR reaction system.

TABLE 4

| | EDTA whole blood concentration/(V/V) | | | | | | | | | | |
|---|---|---|---|---|---|---|---|---|---|---|---|
| | 0 | 10 | 20 | 30 | 40 | 50 | 60 | 70 | 80 | 90 | 100 |
| Buffer A/μL | 0 | 1 | 2 | 3 | 4 | 5 | 6 | 7 | 8 | 9 | 10 |
| Buffer B/μL | 10 | 9 | 8 | 7 | 6 | 5 | 4 | 3 | 2 | 1 | 0 |

Figure 7:
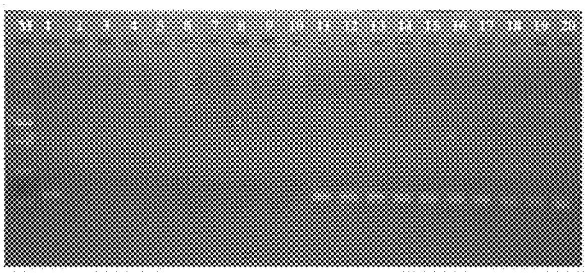
FIG. 7 is a graph showing the results of the wild-type Taq polymerase and Taq-aCb anti-EDTA blood test according to the examples of the present invention.

Taq-aCb was tested for resistance to EDTA whole blood according to the same method as in Example 2, and the results of electrophoresis of the amplified products are shown in FIG. 7.

As in FIGS. 7, 1 to 10 are the PCR product lanes of wild-type Taq polymerase at EDTA blood concentration of 5, 10, 15, 20, 25, 30, 35, 40, 45, and 50% (V/V), respectively; 11~20 are the PCR product lanes of Taq-aCb at EDTA blood concentration of 5, 10, 15, 20, 25, 30, 35, 40, 45, 50% (V/V), respectively.

According to FIG. 7, it can be obtained that the resistance of wild-type Taq polymerase to EDTA whole blood was 5% (volume fraction was calculated based on the volume of blood added to PCR as a percentage of the total volume of the PCR system), and Taq mutant enzyme, Taq-aCb, was 45% resistant to EDTA whole blood, so the Taq polymerase mutant has significantly improved its resistance to EDTA whole blood in comparison with wild-type Taq polymerase.

Example 5: Test of Heparin Whole Blood Resistance of Taq-aCb

Different whole blood concentration gradient solutions (Table 5) were prepared according to the method in Example 2, wherein NaCl in Buffer A was replaced with heparin whole blood, and the volume fraction was calculated according to the volume of blood added to the PCR reaction system.

TABLE 5

| | Heparin whole blood concentration/(V/V) | | | | | | | | | | |
|---|---|---|---|---|---|---|---|---|---|---|---|
| | 0 | 10 | 20 | 30 | 40 | 50 | 60 | 70 | 80 | 90 | 100 |
| Buffer A/μL | 0 | 1 | 2 | 3 | 4 | 5 | 6 | 7 | 8 | 9 | 10 |
| Buffer B/μL | 10 | 9 | 8 | 7 | 6 | 5 | 4 | 3 | 2 | 1 | 0 |

Figure 8:
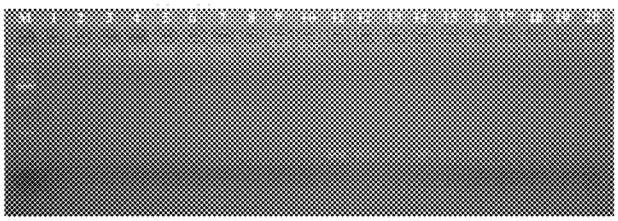
FIG. 8 is a graph showing the results of wild-type Taq polymerase and Taq-aCb anti-heparin blood tests according to the examples of the present invention.

Taq-aCb was tested for resistance to heparin whole blood according to the same method as in Example 2, and electrophoresis results of the amplified products are shown in FIG. 8.

As in FIG. 8, 1-10 are the PCR product lanes of wild-type Taq polymerase at heparin blood concentration of 5, 10, 15, 20, 25, 30, 35, 40, 45, and 50% (V/V), respectively; 11 to 20 are the PCR product lanes of Taq-aCb at heparin blood concentration of 5, 10, 15, 20, 25, 30, 35, 40, 45, and 50% (V/V), respectively.

According to FIG. 8, it can be obtained that the wild-type Taq polymerase has 0% resistance to heparin whole blood (volume fraction was calculated based on the volume of blood added to PCR as a percentage of the total volume of the PCRT system), and the Taq mutant enzyme Taq-aCb has 35% resistance to heparin whole blood, so that the Taq polymerase mutant has a significantly higher resistance to heparin whole blood than the wild-type Taq polymerase.

Example 6: Taq-aCb 5'-3' Exonuclease Activity Test

5'-3' exonuclease activity was assayed by fluorescent probe PCR with wild-type Taq polymerase (ThermoFisher Scientific) as a positive control, diluted to 1U, 2U, 3U, 4U, 5U, and Taq-aCb was similarly diluted to the same activity concentration. The reaction system was prepared as shown in Table 6 below (wherein 10×Taq Buffer was purchased from TaRaKa):

TABLE 6

| Reagent | mixing volume |
|---|---|
| 10X Taq Buffer | 2.5 μL |
| 25 mM $MgCl_2$ | 4.5 μL |
| 2.5 mM dNTPs | 0.2 μL |
| Probe2(10 pmol) | 0.5 μL |
| DNA polymerase test 2(10 pmol) | 0.25 μL |
| ddH2O | 16.05 μL |

PCR reaction conditions: 10 minutes at 95° C., (95° C. for 10 seconds, 55° C. for 30 seconds, read fluorescence)×40 cycles. Using the reaction cycle as the X-axis and the fluorescence value (RFU) corresponding to each cycle as the Y-axis, an RFU-cycling graph was made. The known enzyme concentration was used as the X-axis, and the initial slope corresponding to the RFU-cycling graph was used as the Y-axis to fit the standard curve, and the slope of the linear regression equation obtained could indicate the magnitude of 5'-3' exonuclease activity. The results are shown in FIG. 9.

Figure 9:
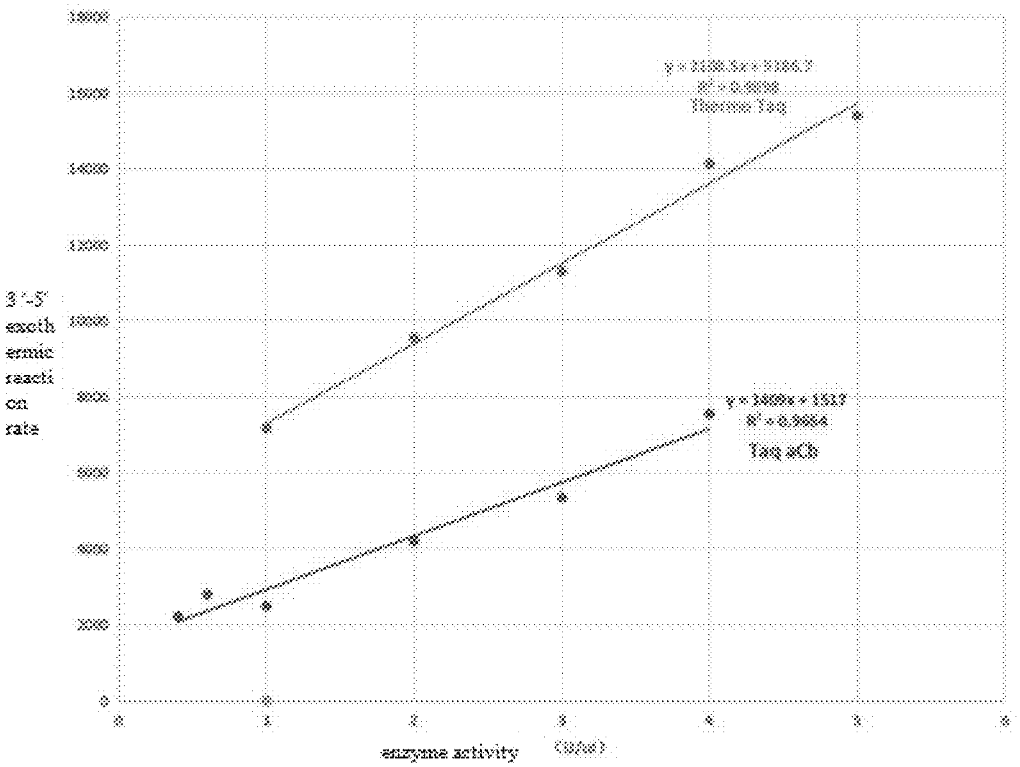
FIG. 9 is a graph of RFU-cycling curves according to Example 8 of the present invention.

According to FIG. 9, the 5'-3' exonuclease activity of Taq-aCb was 66% of that of the wild-type Taq polymerase, which was decreased by the mutation compared to the wild type. It was basically consistent with the wild-type Taq polymerase.

It will be understood by one of ordinary skill in the art that the above embodiments are specific embodiments for realizing the present invention, and that various changes can be made thereto in form and detail in practical application without departing from the spirit and scope of the present invention.

The invention claimed is:

1. A Taq polymerase mutant, wherein the Taq polymerase mutant comprises: the amino acid sequence of SEQ ID NO: 2, wherein the amino acid sequence is mutated at any four or more positions selected from the group consisting of: P40W, L125I, G200M, G499K, E634G and F769I.

2. The Taq polymerase mutant according to claim 1, wherein the Taq polymerase mutant has a resistance to sodium chloride of not less than 70 mM;
- and/or, wherein the Taq polymerase mutant has a resistance to potassium chloride of not less than 100 mM.

3. The Taq polymerase mutant according to claim 1, wherein the Taq polymerase mutant has a resistance to EDTA whole blood of not less than 5%;
- and/or, wherein the Taq polymerase mutant has a resistance to heparin whole blood of not less than 1%.

4. A nucleotide molecule, wherein the nucleotide molecule encodes the Taq polymerase mutant according to claim 1.

5. A vector, wherein the vector contains the nucleotide molecule according to claim 4.

6. A host cell, wherein the host cell contains the nucleotide molecule according to claim 4, or its chromosome is integrated with the nucleotide molecule according to claim 4.

7. A kit, wherein the kit contains the Taq polymerase mutant according to claim 1.

8. A method of preparing a Taq polymerase mutant, wherein the method comprises the steps of:
- (i) culturing the host cell according to claim 6 under suitable conditions so as to express the Taq polymerase mutant; and
- (ii) isolating the Taq polymerase mutant.

* * * * *